United States Patent [19]

Walters

[11] 4,293,912

[45] Oct. 6, 1981

[54] TOMOGRAPHIC APPARATUS

[75] Inventor: Ronald G. Walters, Aurora, Ohio

[73] Assignee: Technicare Corporation, Cleveland, Ohio

[21] Appl. No.: 32,452

[22] Filed: Apr. 23, 1979

Related U.S. Application Data

[62] Division of Ser. No. 838,084, Sep. 30, 1977.

[51] Int. Cl.³ .............................................. G01N 23/08
[52] U.S. Cl. ................................. 364/414; 250/445 T; 364/515
[58] Field of Search ............................ 364/414, 515; 250/363 S, 445 T; 358/111; 340/732

[56] References Cited

U.S. PATENT DOCUMENTS

| | | | |
|---|---|---|---|
| 2,281,931 | 5/1942 | Frank | 250/445 T |
| 2,748,290 | 5/1956 | Reichertz | 250/306 |
| 3,778,614 | 12/1973 | Hounsfield | 250/362 |
| 3,924,129 | 12/1975 | Le May | 250/336 |
| 3,927,318 | 12/1975 | Macovski | 250/272 |
| 3,976,885 | 8/1976 | Brunnett et al. | 250/445 T |
| 4,044,240 | 8/1977 | Cox, Jr. et al. | 364/414 |
| 4,052,619 | 10/1977 | Hounsfield | 250/363 S |
| 4,066,903 | 1/1978 | Le May | 250/445 T |
| 4,071,769 | 1/1978 | Brunnett et al. | 250/445 T |
| 4,114,042 | 9/1978 | Le May | 250/445 T |
| 4,135,247 | 1/1979 | Gordon et al. | 250/445 T |
| 4,138,721 | 2/1979 | Boyd | 364/414 |
| 4,144,570 | 3/1979 | Wagner | 250/445 T |
| 4,149,247 | 4/1979 | Pavkovich et al. | 364/414 |
| 4,149,248 | 4/1979 | Pavkovich | 364/414 |
| 4,168,435 | 9/1979 | Duinker | 250/445 T |

FOREIGN PATENT DOCUMENTS 2521796  11/1976  Fed. Rep. of Germany ...... 364/414

OTHER PUBLICATIONS

Cahill, et al., "The Preliminary Application of a Matrix Inversion Method for Radionuclide Image" (1970), Jnl. of Nucl. Med., vol. 11, No. 10, pp. 613–615.
De Rosier et al., "Reconstruction of 3-D Structures from Electron Micrographs", Nature, vol. 217, Jan. 1968, pp. 130–134.
Cameron et al., "Methods of Bone Mineral in Vivo: An Improved Method"; Science (1963), vol. 142, Oct. 1963, pp. 230–232.
Correspondence, British Journal of Radiology (1973), pp. 314–317.
Budinger et al., "3-D Reconstruction in Nuclear Medicine by Iterative Least Squares and Fourier Transform Techniques" (1974).
Peters, "Spatial Filtering to Improve Transverse Tomography" (1974).
Cho, "Physical and Mathematical Aspects of Transmission 3-D Image Reconstruction".
Logan, "The Uncertainty Principle in Reconstructing Functions from Projections " (1975).
Cho et al., "Computer Algorithm for the Tomographic Image Reconstruction with X-Ray Transmission Scans" (1973).
Cho et al., "Computer Algorithms and Detector Electronics for the Transmission X-Ray Tomography" (1974).
Kalos et al., "Conceptual Design of a Vapor Volume Fraction Instrument" (1961).
Smith et al., "Imagery Construction from Finite Numbers of Projections" (1972).
Bracewell, "Strip Integration in Radio Astronomy" (1956).
Gordon, "A Tutorial on Art" (1974).
Oppenheim, "More Accurate Algorithms for Iterative 3-D Reconstruction" (1974).
Cho, "General Views on 3-D Imagery Construction and Computerized Transverse Axial Tomography" (1974).
Shepp et al., "The Fourier Reconstruction of the Head Section" (1974).
Budinger et al., "3-D Reconstruction in Nuclear Medicine Emission Imaging" (1974).
Ramachandran et al., "3-D Reconstruction of Radiographs and Electron Micrographs: Part III–Descr. and Appl.–Convolution Method" (1971).
Ramachandran et al., "3-D Reconstruction from Radiographs and Electron Micrographs, Appl. of Convolutions Instead of Fourier Transforms" (1971).
Ramachandran, "Reconstruction of Substance from Shadow" (1971).

Cormack, "Representation of a Function by its Line Integrals with Some Radiological Applications II" (1964).
Cormack, "Representation of a Function by its Line Integrals, with some Radiological Applications" (1963).
Nagai et al., "Computer-Focusing Using an Appropriate Gaussian Function" (1968).
Gordon et al., "Algebraic Reconstruction Techniques (Art) for 3-D Electron Microscopy and X-Ray Photography" (1970).
Gilbert, "Iterative Methods for the 3-D Reconstruction of an Object from Projections" (1971).
Cho et al., "Computerized Image Reconstruction Methods with Multiple Photon/X-Ray Transmission Scanning" (1973).
Iinuma et al., "Image Restoration in Radioisotope Imaging Systems" (1967).
Bracewell et al., "Inversion of Fan-Beam Scans in Radio Astronomy" (1967).
Gordon et al., "3-D Reconstruction from Projections: A Review of Algorithms".
Lakshminarayanan, "Reconstruction from Divergent Ray Data", State Univ. of N.Y. at Buffalo, Tech. Report #92, Jan. 1975.

*Primary Examiner*—Errol A. Krass
*Attorney, Agent, or Firm*—Fay & Sharpe

[57] ABSTRACT

The invention relates to the method for constructing a representation of the variation of attenuation of penetrating radiation in a planar slice of a patient positioned in a scan circle. The patient is irradiated with a fan shaped swath of radiation which is rotated about the patient for 180° plus approximately the angle of the fan. Radiation passing through the scan circle is converted to sets of data, each set representing a radiation attenuation across a fan. The sets of data are filtered with a window function to remove data from some of the sets which represent radiation passing through a point in the scan circle by more than 180° relative to radiation paths through the same point. The sets of data are serially convolved and back-projected into an image memory for display on a video monitor. The back projector addresses each set of data by generating subsequent addresses from the previous address and the incremental displacement between adjacent pixels of the image memory using pixel driven algorithms.

33 Claims, 10 Drawing Figures

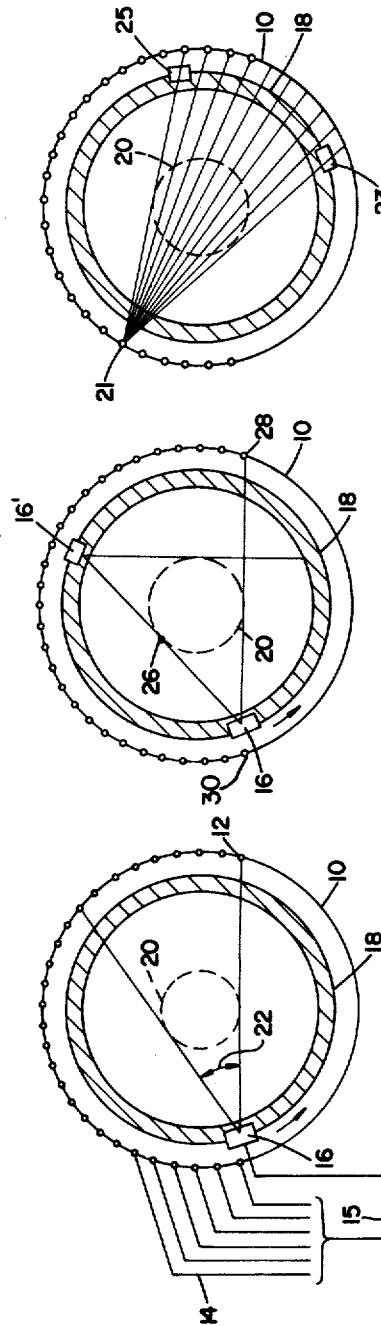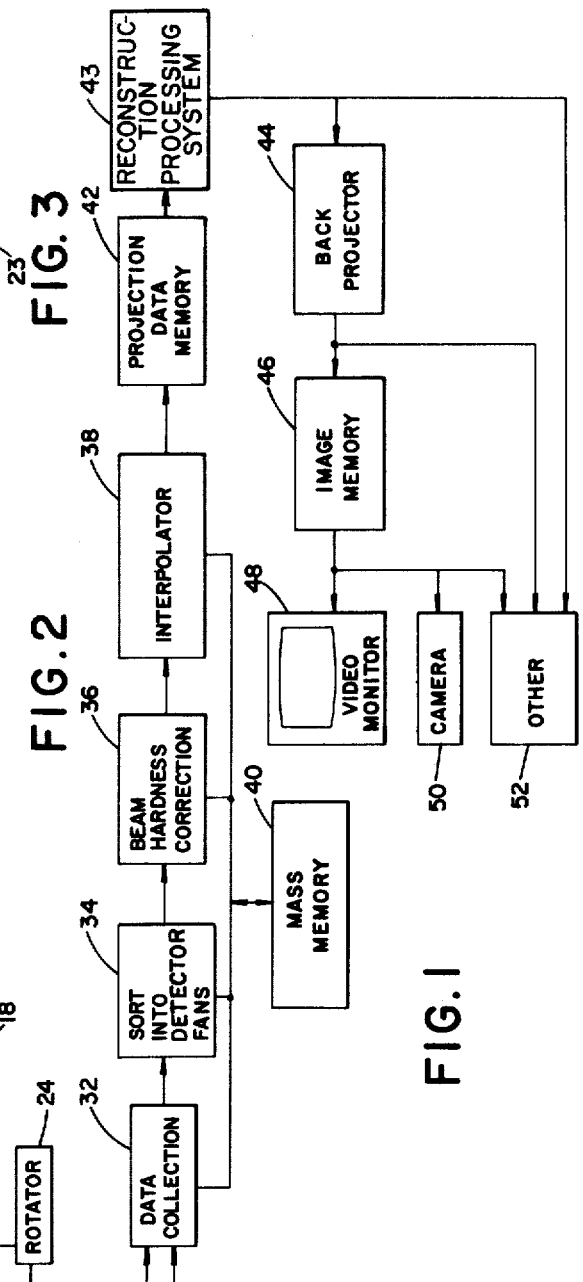

IMAGE COORDINATE SYSTEM

FIRST VIEW $B = -F$
LAST VIEW $B = \pi + F$

TOMOGRAPHIC APPARATUS

BACKGROUND OF THE INVENTION

This application is a division of U.S. application Ser. No. 838,084 entitled X-RAY TOMOGRAPHIC APPARATUS filed Sept. 30, 1977.

This invention relates to the art of medical computerized tomography. This invention has particular application in reconstruction of images from radiation attenuation data taken by rotating fan beam detectors.

There has been a constant trend towards faster and more accurate computerized tomographic scanners. The earliest medical scanners consisted of a source of radiation, such as X-rays, and a detector, the two of which traversed across the body to be examined in a linear manner, then were rotated a few degrees and the traverse repeated. In order to take sufficient readings to reconstruct a tomographic image, several minutes were required. For medical tomography, this length of time was undesirable because it meant holding the patient, and in particular the organ to be examined, totally still for this period of time. This allowed scans to be done on relatively stationary organs, such as the brain, but was not amenable to producing cross-sectional images of rapidly moving organs, such as the heart. Such a system is illustrated in U.S. Pat. No. 3,778,614.

In the quest of great speed, it was found that a fan-shaped beam of radiation could be used which would irradiate a plurality of detectors simultaneously. See for example U.S. Pat. No. 3,881,110. With this apparatus, the traverse motion could be eliminated and the sole motion could be the rotation of the source and detectors. This system increased the speed but also increased the number of detectors—a very expensive component. Further different detectors took readings through different parts of the body. To sum these together, it was essential that each detector be and remain equally sensitive lest the sensitivity difference give the appearance that more or less radiation was being absorbed by that part of the body.

The next step in increasing the speed was constructing all the detectors to be stationary with a single rotating source (see U.S. patent application Ser. No. 726,556, assigned to the U.S. Department of Health, Education and Welfare). Although this increased the speed, it required detectors to be placed 360° around the patient.

Some rotating fan beam scanners (see, for example, U.S. Pat. No. 4,031,395, the embodiment of FIG. 3) process the attenuation data as if it were traverse and rotate data acquired in a different order. These scanners have an inaccuracy in that the attenuation data acquired by a rotating fan beam scanner does not exactly duplicate the data of a traverse and rotae scanner. Rather, some approximations must be made in binning the fan beam data into parallel ray data. Other scanners reconstruct the image by processing the data with algorithms particularly suited to rotating fan beam scanners, see the article *Reconstruction from Divergent Ray Data*, by A. V. Lakshaminarayanan in "Technical Report No. 92", State University of New York at Buffalo, Department of Computer Science, Jan., 1975. This reconstruction technique is faster and more accurate. But heretofore, it was believed that 360° of views were required in the rotating fan beam reconstruction system, see page 7, supra, hence enough detectors to encircle the full 360° of the patient circle.

The present invention is a major breakthrough because it recognizes for the first time that 360° of views need not be taken in divergent fan beam geometry. Instead, the present invention recognizes that every point within the area to be examined need only be viewed from 180° of angles in order to produce a complete set of projection data. This, in turn, enables the system to operate much faster because the X-ray source need only scan a little over 180°. Additionally, the present system is more economical because it eliminates nearly half the detectors that would be needed in a 360° scan system.

The speed with which the patient was scanned was not the only concern with early computer tomographic devices for medical use. The earliest units were very slow in producing images and the images that they produced were not as sharp and clear as would be desired. The early traverse and rotate systems, in effect, took a series of density readings as they traversed and then filled sequential columns of a matrix with the sequential density readings. When the system rotated and traversed again, it would fill a second matrix. These matrices were then stacked, each rotated at an angle relative to the other, and the intensities at the corresponding point of each matrix, i.e. each vertical column of intensities, were summed. This was a slow system and less than accurate.

Then it was discovered that if each sum of intensities were to some degree, modified by its surrounding intensities the image could be refined. However, these methods were even more time consuming, often requiring as much as fifteen minutes for a computer to transform the data into a tomographic image.

The next step towards speeding up the processing of data into images was to modify the intensity at each detector by the intensities read on the surrounding detectors before summing intensity values into the matrix. See, for example, U.S. Pat. No. 3,924,129. The system shown uses a number of geometrically derived approximations to make these modifications.

Additionally, articles have been published which advocate convolution theory to modify the intensity at each point as a function of its surrounding points. These all multiply the intensity data at a given point by a convolution function whose values are determined by the intensities read at surrounding points. The convolved intensity data is then stored in matrices for processing into an image representation. The convolution method is faster than the geometric method because functions are brought together as a unit rather than a series of individual point calculations. However, as pointed out above, regarding the Lakshaminarayanan article, it has heretofore been believed that the convolution integral need be from 0 to 2 $\pi$ radians, i.e. that absorption intensities must be read through 360° around the patient.

An advantage of the present invention is that it reduces the image processing time by not processing redundant data. Rather it only processes views which surround each point of the object to be viewed by 180°.

A further advantage of the present invention is that it includes a faster back projection system. The back projector works with data in the same order as the convolver, hence the back projector can back project the data into the image memory as it emerges from the convolver.

Another advantage of the present system is that each detector receives absorption data along paths passing through the entire body. Hence, if all detectors do not have precisely the same sensitivity, the differences will be averaged out without causing an error in the final tomographic image.

Another advantage of the present system is that it has a convolver function which provides a greater resolution, faster processing and simpler calculations all from fewer views.

The present invention contemplates new and improved tomographic scanners which overcomes the above problems and others and provides faster scanning and image reconstruction.

SUMMARY OF THE INVENTION

The invention relates to an X-ray tomographic system which consists of a radiation source such as gamma ray or X-ray radiation which produces a fan beam of radiation. The fan is wide enough to encompass the patient circle. The system further includes means for rotating the radiation source about the patient circle for less than a full rotation. Further, there is detection means for detecting the radiation at positions which surround the patient circle by 180° plus the angle of the fan beam plus the angle between the adjacent fan detectors. In the preferred embodiment, this is about 215° for a patient circle of 50 cm. Attenuation data from the detectors is sorted into detector fans of attenuation data. This data then is processed including convolving it with a convolver function. The convolved data is then back projected into an image memory and displayed on a video monitor.

Another aspect of the invention is the reconstruction of an image. Sets of data each set representing a characteristic of attenuation of a fa-shaped swath of radiation at a plurality of angular orientations spanning an arc of more than 180° but less than 360° are convolved with a convolution function. The convolved sets of data are transformed into a representation of a planar slice of the examined object.

Another object of the invention is the construction of a representation of variations in radiation attenuation in a planar slice of a body. Sets of data representing radiation attenuation by an array of radiation beams are combined with a filter function to edit redundant data. The edited data sets are back projected into an image memory from which an image may be produced.

Another aspect of the invention is the back projection of sets of data into an image memory. For each pixel position in the image memory, singly but following an S-like path through the image memory, an address in each set of data is determined. The data value corresponding to the determined address is multiplied by a weighting function and added to the image memory at an address corresponding to the pixel position.

DESCRIPTION OF THE FIGURES

The invention may take physical form in certain parts and arrangement of parts a preferred embodiment of which will be described in detail in this specification and illustrated in the accompanying dawings.

FIG. 1 is a block diagram of a system in accordance with the present invention;

FIG. 2 illustrates a geometry of detectors, X-ray source and fan beams in illustration of the present invention;

FIG. 3 illustrates a detector fan for a random detector;

DESCRIPTION OF THE PREFERRED EMBODIMENT

Figure 4:
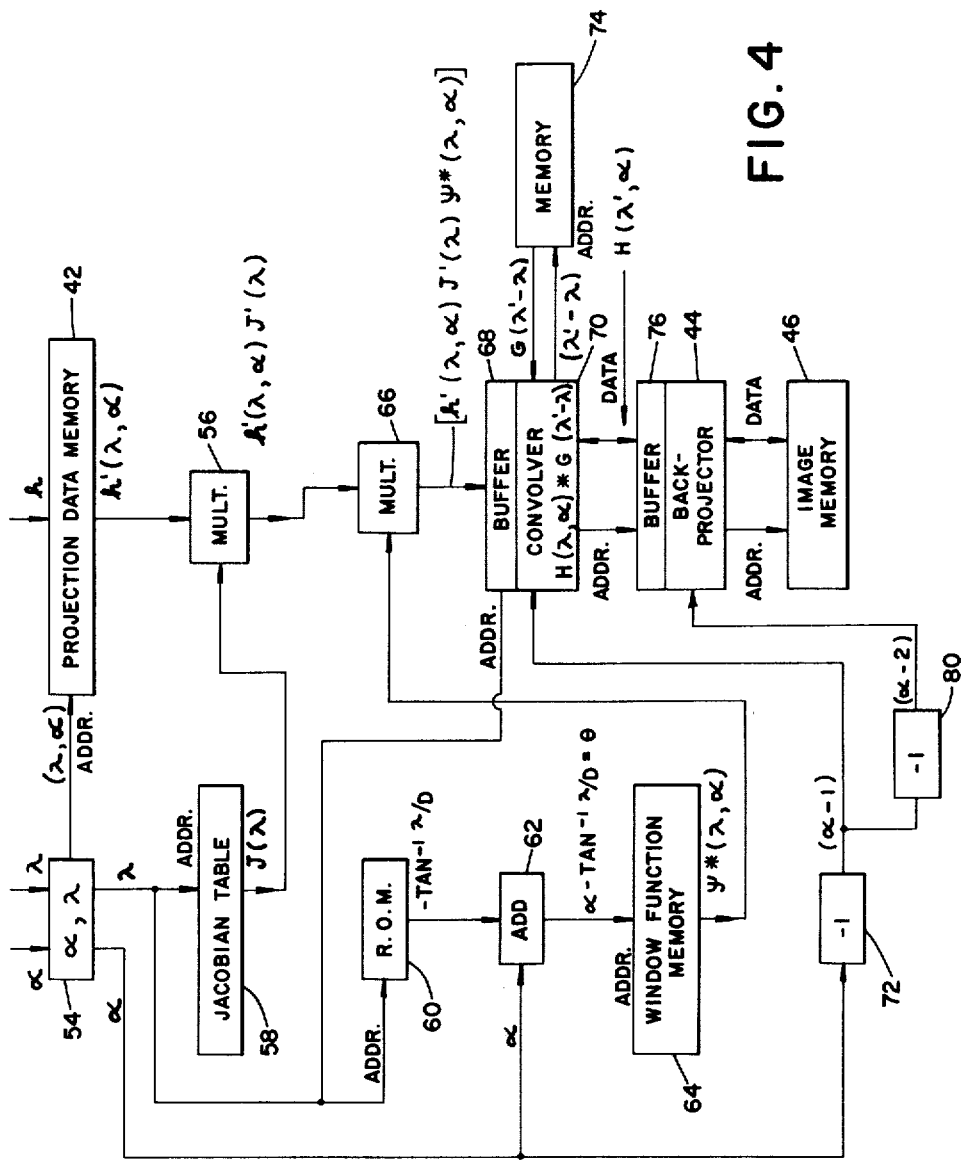
FIG. 4 is a block diagram of processing hardware converting the projection data into convolved data and then projecting it into the image memory.

FIG. 1 illustrates an overall system diagram. The apparatus for performing a physical examination of a patient with radiation consists of a stationary frame 10 upon which is mounted an array of X-ray detectors 12. These detectors may be individual scintillation crystals and photomultiplier tubes, or they may be the ends of light pipe which connect one or several detector stations to a single photomultiplier tube or they may be solid state detectors. Radiation detection means, including detectors 12, detects radiation and produces electronic data signals indicative of the intensity of the radiation impinging upon the detector. Because the intensity of the X-rays was known at the source, the intensity of the X-rays impinging upon an individual detector is representative of the attenuation of the X-ray beam along the path between the source and the detector, i.e. the attenuation by the components in elemental regions of the patient's body located along that path. The electrical signals indicative of this intensity from the individual detectors are conveyed along electrical lines 14 to a processing means.

The apparatus further includes an X-ray source 16 which produces a fan-shaped beam or swath of X-rays. There is a means 24 for rotating the X-ray source around a scan or patient circle 20 and monitoring the angular position of the source. A means 18 constrains the X-ray source to rotate along an arc segment of a circle's circumference. It will be noted that the detectors 12 are arranged only around a part of the circumference of the device. The X-ray source only rotates a similar number of degrees about the patient circle.

Looking to FIG. 2, the geometries of the device will become much clearer. The present invention has found that examining each point of the object being examined around an arc of 180° provides a complete set of data to make a tomographic image. Examining any given point for more than 180° provides redundant data which is removed. The reconstruction technique of the Lakshaminarayanan article supra, by taking 360° of data, apparently unbeknownst to the author, took two complete sets of data and averaged them. Accordingly, the geometry of the system should be such that a point 26 on the circumference of the scan circle is examined from a full 180°, but no more. In order for this to occur, the X-ray source must move from its first position 16 counterclockwise around the scan circle to end position 16'. Similarly, only so many detectors 12 are provided as needed to receive data around 180° of all points in the scan circle. It is readily apparent that the detectors need only extend from a point 28 counterclockwise around the exterior of the device to a point 30. any detectors on a lower side of the circle clockwise between points 30 and 28 would produce redundant views which are only filtered out before the signals are processed. It will be seen that the exact number of degrees around the outer circumference which must be provided with detectors will vary the geometry of the system. It will vary with the relative diameters of the scan circle and the detector circle as well as the circle around which the X-ray source rotates. As the diameter of the scan circle approaches zero, the number of degrees around which detectors need be provided approaches 180°. It will further be seen that for a fan beam of X-rays with an angle 22 just sufficient to span the entire scan circle, that if the radius about which the X-ray source rotates is the same as the radius about which the detectors are located, then the detectors may be located around 180° of the circumference plus the angle 22 of the X-ray source. In the preferred embodiment, the X-ray source rotates about a radius slightly smaller than the radius about which the detectors are arranged, so the number of degrees about which the detectors must be placed is just slightly less than 180° plus the angle of the source fan beam. Further, as a practical matter, the detectors are not a continuum but a series of discrete points. Thus, the source rotates yet an additional angular amount equal to the angular spacing between detector elements in order to assure that every point of the patient circle is viewed from at least 180°. If, for example, the detectors were spaced 4° apart, then if the X-ray source were rotated just far enough to subject point 26 to radiation from 180° different degrees, it is possible that because of the 4° spacing between detectors, data might only be received representing 176° of views about point 26.

Viewing the system from the point of a detector 21 of the array of detectors 12, FIG. 3, it will be seen that detector 21 receives X-rays the entire time which X-ray source 16 is located between positions 23 and 25. However, with digital processing equipment, as the preferred embodiment uses, a continuum of intensity versus time is not readily processed. Accordingly, the amount of attenuation of the X-rays reaching detector 21 is measured periodically as the X-ray source traverses the arc between points 23 and 25, each sampling of detector 21 by the processing means representing the attenuation along a path through the scan circle. The angular spacing of these paths determines the resolution of the final tomographic image and may be as closely spaced as the physical limitations of the processing equipment will allow. Thus, although every detector is capable of producing a continuum of X-ray attenuation of data, digital data processing equipment only takes a discrete number of X-ray attenuation samplings of each detector.

Looking again to FIG. 1, wherein the processing means is further illustrated. It is connected to the detectors by lines 14 for processing a representation of the radiation attenuation in the scan circle and is connected with means for displaying or storing the representations. Each time the array of detectors are sampled, an element of attenuation data from each detector that is irradiated is conveyed along one of lines 14 to the data collection means 32 which forms digital representations of the log of each detector's output. Each detector sampling, it will be apparent, represents attenuation data collected along one of the paths in the fan-shaped continuum of paths received by each detected element discussed above in reference to FIG. 3. A second signal along line 15 representative of the angular position of the X-ray source is also conveyed to data collector means 32 so that each attenuation reading is coordinated with the angle through the patient at which it was taken. The data as the log of the intensity is temporarily stored in a mass memory 40 until at least one of the detector means has received all the attenuation data which it will receive. At this time, a sort means 34 starts reorganizing the data into sets of data arranged by detector fan beams. That is, all the attenuation data taken by a single detector along all angles is arranged in order as one set of attenuation data. Thus, the sort means 34 reorganizes the data from source fan beam data sets into detector fan beam data sets but does not bin the fan beam data sets into parallel ray data sets. The data is then corrected by a beam hardness correction means 36 which averages several data values of each set of data corresponding to the edge of each detector fan and subtracts the average from the set of data values thereby correcting the detector for gain drift. Following this, each data value is modified by a non-linear operator for beam hardness correction and fed into an interpolator means. Means 38 interpolates a set of data into equal tangents (see equation #17 to follow) and feeds this information into a projection data memory 42. As each set of data corresponding to a detector fan is processed, it is addressed into a reconstruction processing system 43, which is explained below in conjunction with FIG. 4. The reconstruction processing system adjusts the data for angular position, removes redundant data elements from some sets of data and convolves the data with a convolution function. Taken together the apparatus from the radiation source through to the reconstruction processor comprise a means for generating a plurality of sets of data, each set representing a characteristic of the attenuation of radiation. This process is repeated for each set of data.

After each set of data is convolved by the convolving means to form a convolved set of data, the convolved data is processed by a means for transforming the convolved sets of data into representation of the planar slice of the patient irradiated. This transforming means includes a back projecting means 44, image memory means 46 and display means such as a video monitor 48. Back projector 44 along with image memory 46 transforms the convolved data into a series of intensity representations for each pixel along the raster scan of a video monitor. Also connected with image memory 46 may be a camera means 50 such as the camera marketed under the trade name DELTA-MAT by Ohio-Nuclear, Inc. of Solon, Ohio. Additionally, other storage or display means 52, such as a video recorder, may be connected with the system.

FIG. 4 is a block diagram of the reconstruction processing system 43. It will be noted that every beam path can be uniquely described by the angular position of the detector which detected it, and the angle within the detector fan. This angle can also be expressed as a function of that angle such as its tangent. A means 54 receives two input signals, $\alpha$ which indicates the angular position of the detector and $\lambda$ which represents the tangent of the angle of the path within that detector's fan. The projection data identified as h or $h(\lambda,\phi)$ is an intensity or attenuation of the radiation along each beam path $(\lambda,\alpha)$. The projection data is fed into projection data memory 42. In the timing sequence, each successive value of $\lambda$ for a given $\alpha$ along with the corresponding projection data h is read in and processed until each $\lambda$ for a given fan has been processed through. At that time, the system moves on to the next detector, reads a new angle α, and starts indexing the λ's and h's through the system again. Projection data memory 42 contains the projection data indexed by α the fan angle and λ the tangent of the angle within the fan. Typically, memory 42 is a RAM capable of storing all the fans, or in the situation in which data collection is slower than processing speed, a double buffer may be used. Means 54 addresses the α and λ values being read to the projection data memory 42 which in turn feeds out the appropriate attenuation data h' (λ,α) to a multiplier 56.

A Read Only Memory 58 is pre-programmed with a Jacobian table and is addressed by λ. For each value of λ, there is a value stored within this table. For the mathematical function which is chosen for use in the preferred embodiment, the Jacobian equals Cos$^3$ (arctan (λ/D)), where D is the distance from the apex of the detector fan to center of the scan circle. Multiplier 56 multiplies projection data h'(λ,α) by the Jacobian obtained from the Jacobian table 58.

A Read Only Memory 60 contains a table of arctangents. Read Only Memory 60 is addressed by each λ and produces on its output a value equal to -arctan (λ/D). An Adder 62 combines the angle α with the output of Read Only Memory 60 to produce the sum which is α-arctan λ/D.

As indicated earlier, each point within the scan circle should be viewed from only 180°, no more. The redundant data provides more values for some points in the scan circle than others which causes errors in the final tomographic projection. Accordingly, it is necessary to filter out the surplus values. From the geometry of the system, it is clear that certain values of α-arctan (λ/D) will represent a redundant value, whereas others will not. Accordingly, the generating means includes a window means for editing redundant data signals from the sets of data signals. It includes a window function memory 64 which stores a window function ψ* (λ,α) which may be written as:

$$\psi^*(\lambda,\alpha) = \int_{-F}^{\pi+F} \psi(\lambda,\beta)\Lambda(\alpha,\beta)\,d\beta$$

where $\psi(\lambda,\beta) = 1$ if $0 \leq \beta\text{-arctan}\frac{\lambda}{D} \leq \pi$ $= 0$ otherwise See the discussion surrounding equation (24) to follow. β is the angular displacement about the body as is α, however, the variable β can take a continuum of values whereas the variable α is defined only to take discrete values corresponding to detector positions. An example of an interpolation function Λ(α,β) which can be used is:

$$\frac{\sin(\pi(\alpha,\beta)/b)}{\pi(\alpha,\beta)/b}$$

where b is the spacing between views, i.e. spacing between detectors. Thus, all the values of the equation are known, and according with the predetermine program for each value of (α-arctan λ/D) a value of ψ* (λ,α) is produced.

The window function ψ* goes to multiplier 66 where the output of multiplier 56 is multiplied by the window function to produce the product of the projection data times the Jacobian times the window function, i.e. h'(λ,α)J(λ)ψ*(λ,α). For simplicity, this product will be referred to as H(λ,α).

A Buffer 68, as indicated above, is optional and need not be used unless the data collection speed is slower than the processing speed. A Convolver 70 is a conventional convolver whose input may be double buffered by buffer 68 to allow overlapped convolution and back projection. Adder 72 changes the angle α to (α−1), i.e. indexes the α to the angle of the preceding detection fan. Buffer 68 is addressed by λ and convolver 70 receives the input indicative of (α−1). Memory 74 contains a table of values for a convolution or filter function called G(λ'−λ) which is addressed by convolver 70 for different values of (λ'−λ) to provide an output function G(λ'−λ) which is convolved in convolver 70 with function H(λ,α). The value of H(λ,α) for specific values of λ and α is convolved with a convolving function G(λ'−λ):

$$H(\lambda',\alpha) = H(\lambda,\alpha)*G(\lambda'-\lambda)$$

That is, for a data line that is sampled periodically, the convolved data at the Mth sampled position on a data line α is:

$$H(M,\alpha) = \sum_{N=-\rho^*}^{\rho^*} H'(N,\alpha)^* G(M - N).$$

A wide choice of convolution functions may be used such as the one shown by Lakshminarayanan, supra in which $G(M - N) = 1$ when $M - N = 0$ $= \dfrac{4}{\pi^2(M - N)^2}$ when $M - N$ is odd $= 0$ when $M - N$ is even Other functions such as shown in U.S. Pat. No. 3,924,129 could be used instead.

The data from convolver 70 is addressed and fed into a buffer 76, which is used in conjunction with back projector 44. The workings of the back projector will be further explained in conjunction with FIGS. 5 and 6.

There are several ways in which the back projection operation may be accomplished, see for example U.S. Pat. No. 3,924,129. The most desirable techniques, however, are those resulting in pixel driven algorithms, i.e. algorithms in which the matrix element location is the independent variable. The process herein not only uses such an algorithm, but also does not require tangent calculations. The present invention develops a simple set of linear relationships between the detector fan sets of data and image matrix which permits the back projection to be described by a set of differential equations which may be implemented with a minimal amount of calculation. Minimizing the amount of calculation is very important because back projection requires on the order of the number of projection lines cubed of iterations and is generally the most time consuming part of reconstruction. Referring now to the mathematical derivation section to follow, it will be seen that the following is a description of the reconstruction process:

$$f(r,\phi) =$$

-continued $$\frac{D^2}{4a} \sum_{\alpha=-\infty}^{\infty} \sum_{\lambda=-\rho^*}^{\rho^*} h'(\lambda,\alpha) \cos\left(\arctan\frac{\lambda}{D}\right) \frac{1}{(\kappa \cos \mu)^2} G(\lambda' - \lambda)\psi^*(\lambda,\alpha)$$

Because $1/(\kappa \cos \mu)^2$ is a function only of R, $\phi$, and $\alpha$, it can be brought out of the inner summation. Accordingly, the equation can be rewritten as follows, where the inner summation has already been accomplished in convolver 70:

$$f(r,\phi) = \frac{D^2}{4a} \sum_{\alpha=-(F+A)}^{\pi+F+A} \frac{1}{(\kappa \cos \mu)^2} \sum_{\lambda=-\rho^*}^{\rho^*} h'(\lambda,\alpha) \cos(\arctan \lambda/D) G(\lambda' - \lambda)\psi^*(\lambda,\alpha)$$

Figure 5A:
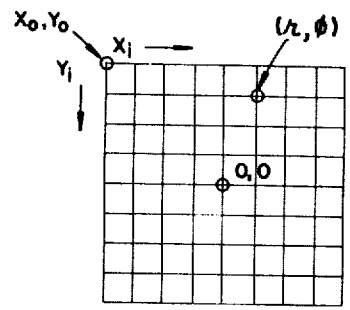
FIG. 5A illustrates the Cartesian coordinate system of the image memory.
Figure 5B:
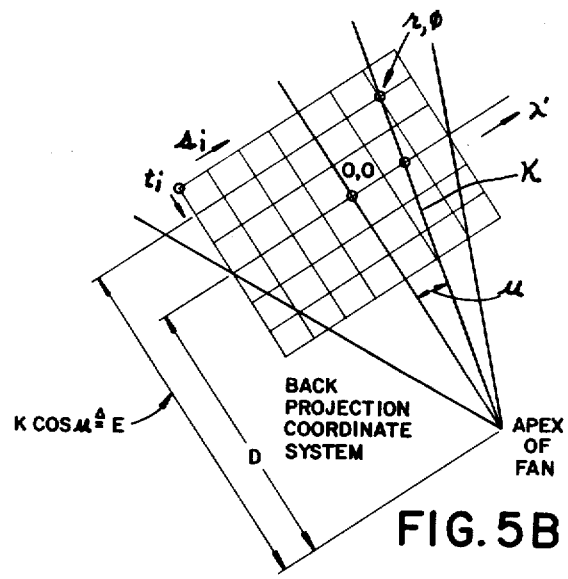
FIG. 5B illustrates a rotated Cartesian coordinate system for some selected fan beam.
Figure 7:
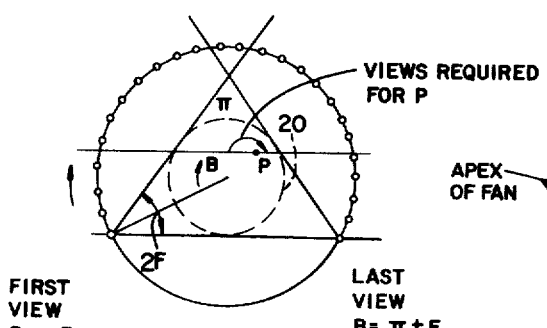
FIG. 7 illustrates 180° plus fan beam geometry.

FIGS. 5A and 5B show the relationship between the Cartesian image matrix and the geometry of FIG. 3. This relationship has been simplified in FIG. 5B by superimposing another Cartesian coordinate system (s,t) which is rotated into alignment with the divergent system. The description of $\kappa(r,\phi,\alpha)$ and $\mu(r,\phi,\alpha)$ is simplified by transforming from the (x,y) coordinate system to the (s,t) coordinate system. Using these systems in the relation shown in FIG. 5B, the above equation can be written in these variables as follows:

$$F(x,y) = \frac{D^2}{4a} \sum_{\alpha=-F-A}^{\pi+F+A} \frac{1}{E^2(x,y,\alpha)} H(\lambda',\alpha)$$

where $$E(x,y,\alpha) = D + X \sin \alpha + Y \cos \alpha$$
$$\lambda' = (X \cos \alpha - Y \sin \alpha)/E(x,y,\alpha)$$

where, of course, the above equations describe the operations to be performed by the back projector. It will be noticed that the system will work with traverse and rotate type scanning such as shown in U.S. Pat. No. 3,924,129 but is best suited to the fan beam type X-ray source.

The system computes and indexes $\lambda'$ into the convolved data $H(\lambda',\alpha)$, weights by $1/E^2$ and sums into the appropriate matrix point. It can be seen that a simple linear relationship exists with the determination of E and $\lambda'$. In fact, the equations above for $E(x,y,\alpha)$ and $\lambda'$ may be processed by finite differences in order to reduce the multiplications required.

For example, if one were to proceed through the matrix in the x direction, these equations become:

$$E_{J+1} = E_J + \frac{\partial t}{\partial x}$$
$$\lambda'_{J+1} = s_J + 1/E_{J+1}$$
$$s_{J+1} = s_J + \frac{\partial s}{\partial x}$$

where $$\frac{\partial t}{\partial x} = \sin \alpha; \frac{\partial s}{\partial x} = \cos \alpha$$

Similar equations would result proceeding through the matrix in the y direction.

Figure 6:
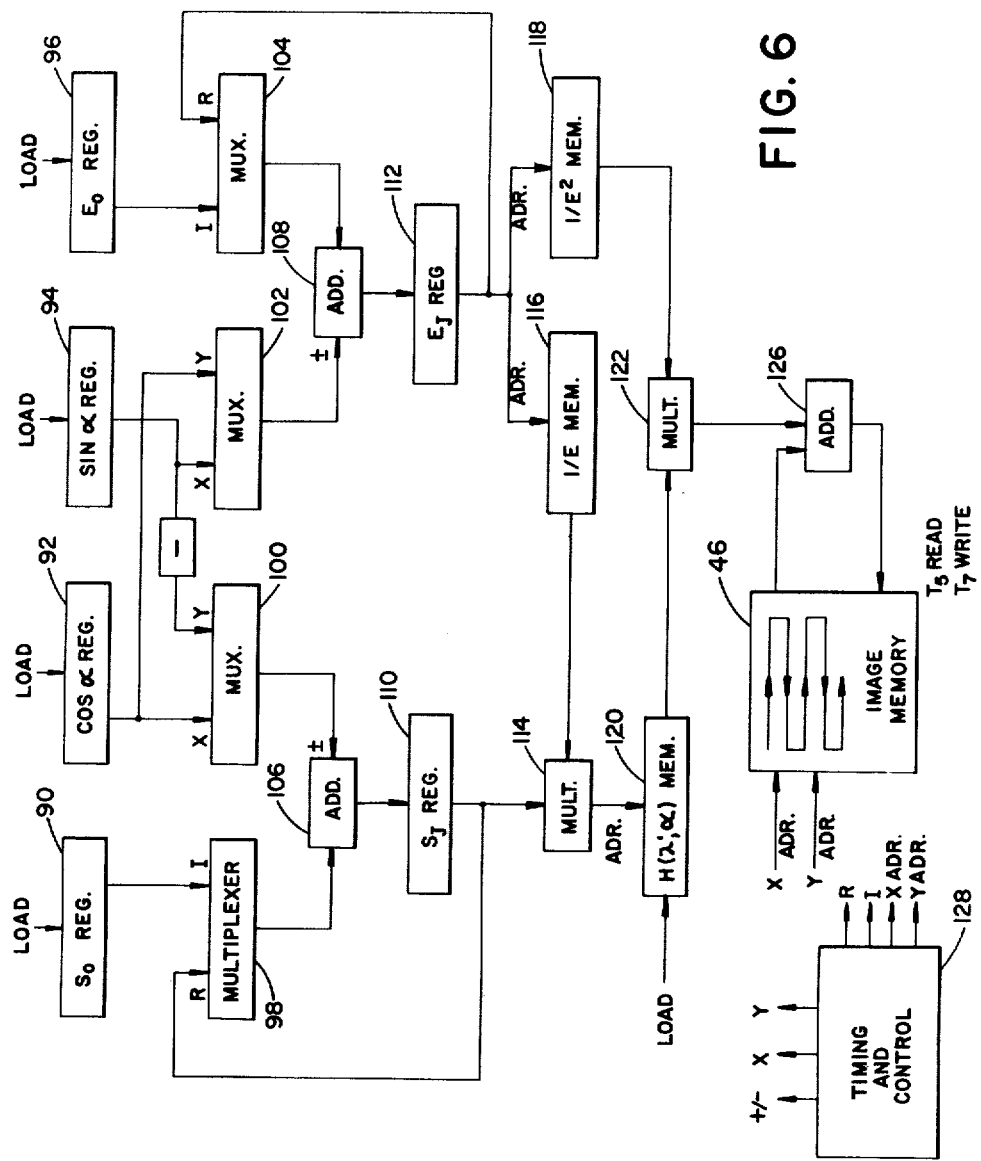
FIG. 6 is a block diagram of a back projection system in accordance with the present invention.

FIG. 6 is a block diagram of the back projector system. All the operations are shown as sequential, however, with the use of latches, the operations may be pipelined causing multiplies and memory accesses to be overlapped, significantly increasing the speed of these operations.

A host processor loads the value $\alpha$ describing the orientation of a single projection line into registers 92 and 94. The values $s_o$ and $E_o$ are determined by the computations above.

For each detector position, i.e. view angle $\alpha$, multiplexers 98 and 104 are initialized with input I and an $s_J$ register 110 and an $E_J$ register 112 are cleared. In the run mode, the "R" input to multiplexers 98 and 104 is selected so that the $s_J$ register 110 and $E_J$ register 112 can be incremented. Timing and control means 128 initiates this incrementing each time it advances the address in the image memory by one position. The contents of the $s_J$ register 110 and the $E_J$ register 112 are increments so that they progressively contain the value of $s_0$, $s_1$, $s_2$, etc. and $E_o$, $E_1$, $E_2$, etc. A Memory 116 and a memory 118 may be ROM or RAM memories. If a RAM is used, the host processor could alter the geometry of the processor by loading different tables. These memories are reciprocal tables for E and $E^2$. For each value of E, memory 116 puts out the value of one over E and memory 118 puts the value of one over $E^2$.

Multiplier 114 performs the multiplication set forth in the equation for $\lambda'$, i.e. forms the data address $\lambda'$ into the projection data. A memory 120, e.g. a RAM, stores projections data $H(\lambda',\alpha)$ supplied by convolver 70 of FIG. 4. This describes a means for selecting data addresses in each set of data stored in memory 120 corresponding to memory address of the image memory. This projection data may be loaded into memory 120 from the convolver 70 directly or by a host processor.

As was the case in the processing equipment shown in FIG. 4, the back projector for given angle $\alpha$, i.e. for a given detector position, processes each of the possible beam paths $\lambda$ within the view angle before going on to the next angle $\alpha$. Accordingly, the back projector need not wait until the convolver has processed data lines or sets of data for all angles of $\alpha$ but need wait only to the end of the convolving of the data line for a first angle $\alpha$ to form a set of convolved data before making the back projection entries in image memory 46. For detector position $\alpha$, each time the memory 120 is addressed by $\lambda'$, the memory functions as a means for determining the data value for the selected data address and produces an output signal indicative of the convoluted data $H(\lambda',\alpha)$.

A Multiplier means 122 multiplies the output of memory 120 by a weighting function from memory 118. This, in effect, weights the projection ray $H(\lambda',\alpha)$ by one over $E^2$, which is the value to be superimposed on a given matrix point. An Adder means 126 combines this value with the current contents of the corresponding matrix position in image memory 116. This process continues until all the projection data has been convoluted and back projected into the image memory. At this time, the contents of the image memory are effectively the tomograph of the cross section involved.

It is convenient for image memory 46 to be a matrix having the same number of lines as there are raster scan lines on a standard TV monitor, i.e. 512, and to have as many matrix points along each line as there are data points along each raster scan, e.g. 512. With a digital-to-analog converter and a standard TV monitor the contents of the image memory can be transformed into a video picture.

In some instances, it is desirable to interpolate the projection data during back projection. This can be done by addressing the two nearest points in the H($\lambda'$,$\alpha$) memory 120, by obtaining addresses with fractional parts, or by using another adder and multiplier to form a linear interpolation at the output of the memory. This, however, can be costly in hardware and processing time. A more convenient way is to pre-interpolate H($\lambda'$,$\alpha$) in a host processor to produce a longer data line then compute correspondingly high precision $\lambda'$ addresses into memory 120. Although this requires a larger memory 120, it has a computational advantage in that interpolation is done once per view, $\alpha$, rather than approximately once per image matrix line per view, e.g. 512 times per $\alpha$ data line.

In some cases, the back projector may be faster than the generally large image memory, causing the processor to be input-output bound. This can be resolved by buffering several sets of projection data in a fast memory and buffering one or more image memory lines in fast memory. In this way, several views can be projected into each image line before a transfer is made into the image memory. This increases the effective speed of the image memory by an amount proportional to the number of projection lines buffered.

The next section will describe the mathematics behind the reconstruction algorithm of the preferred embodiment. It will, of course, be understood that the equipment described in FIG. 4 can operate with other convolution functions although this might require changing the values in some of the tables in some of the memories, and the convolution function to be described can be used with other equipment. For example, a multi-purpose digital computer or microprocessor could be used. Further, the back projection system can be used independently of the convolution function or the hardware of FIG. 4, and conversely other back projectors can be used with the hardware of FIG. 4 and/or the convolution function to be described in the following.

Mathematical Derivation

Figure 8:
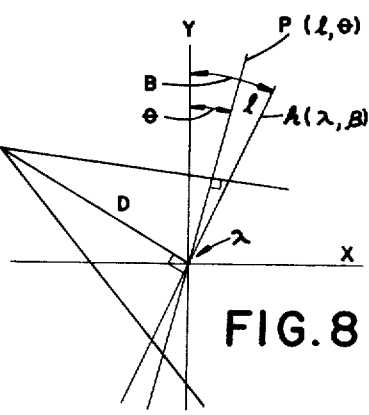
FIG. 8 is a geometric illustration showing a change in coordinates.

This mathematical derivation will view the system from the point of view of a detector element, such as detector 21 shown in FIG. 3. If a line h($\lambda$,$\beta$) were drawn as shown in FIG. 8 perpendicular to the center ray of the fan, then all the lines of the fan would intersect that line. Each beam within the fan has a single value indicative of the attenuation along the beam path. If this value were applied to line h in FIG. 8 at the point at which each fan beam crossed it, then line h would have a series of amplitudes indicative of the attenuation along the ray which crossed the line at each point. These individual discrete amplitudes can be interpolated into a smooth continuous function. In this manner then, line h can be said to be the data line for this fan view of the object examined. The value along any point on line h can be addressed by knowing the apex of the detector fan (i.e. detector position) which is defined by angle $\beta$ and the angle within the fan which is equivalent to defining a position along line h indexed by $\lambda$. Angle $\beta$ related to angle $\alpha$, above, in that both represent the angular position of the apex of a fan. However, unlike angle $\alpha$ which takes only the discrete values correspond to actual physical detectors 12, angle $\beta$ is a mathematical variable which defined as a continuous function. Earlier tomographic systems employed a traverse and rotate system in which the detector viewed the attenuation along a set of parallel beam paths, then was rotated and viewed another set of parallel beam paths at some angle to the first set, etc. For any given object, projection data from the traverse and rotate system, is the same as the projection data from the rotating fan beam system. The individual data points and actual beam paths will be different but the totality of the data will provide the same image. Where p(l, $\theta$) is the projection data for traverse and rotate system, the relationship between the traverse and rotate system and rotating fan beam system can be expressed as $$p(l,\theta) = h(\lambda,\beta) \tag{1}$$

where, looking to FIG. 8, simple geometry shows the following relationships:

$$\theta = \beta + \tan^{-1}(\lambda/D) \tag{2}$$

$$l = \lambda \cos \tan^{-1}(\lambda/D) \tag{3}$$

thus, the projection data for the rotating fan beam system can also be expressed as:

$$h(\lambda,\beta) = p(\lambda \cos(\tan^{-1}(\lambda/D), \beta + \tan^{-1}(\lambda/D)) \tag{4}$$

From the central section thereon, it is known that for a point to be reconstructed:

$$f(r,\phi) = \int_0^\pi \int_{-\infty}^\infty |R| F(R,\theta) \exp[2\pi i R r \cos(\theta - \phi)] \, dR d\theta \tag{5}$$

where f(r,$\phi$) is a two-dimensional image in real space which is to be reconstructed and wherein r and $\phi$ are the polar coordinates for the points in real space and where F(R,$\theta$) is a fourier transform where R and $\theta$ are the polar coordinates in fourier space. It will be noted that the central section theorem is expressed with different limits than the limits shown in the article by A. V. Lakshminarayanan, supra. The proof, to follow, will show that it is only necessary to integrate from 0 to $\pi$ and not as Lakshminarayanan pointed out on page 7 of his article from 0 to $2\pi$. In polar coordinates integrating from 0 to $2\pi$ for the angular displacement and zero to infinity for the radial displacement is the equivalent of integrating from 0 to $\pi$ for the angular displacement and minus infinity to plus infinity for the radial displacement, since both sets of integrals sample all the same points.

The fourier transform of f(r, $\phi$) is related to the projection by:

$$F(R,\theta) = \int_{-\rho}^{\rho} p(l,\theta) \exp(-2\pi i R l) dl \tag{6}$$

or inserting the relationships set forth in equations (2), (3), and (4) into equation (6), it can be rewritten:

$$F(R,\theta) = \int_{-\rho^*}^{\rho^*} h(\lambda, \theta - \tan^{-1}\lambda/D) \exp[-2\pi i R\lambda \cos(\tan^{-1}\lambda/D)] J(\lambda) d\lambda \quad (7)$$

$$f(r,\phi) = \int_{-\infty}^{\infty} \int_{-\rho^*}^{\rho^*} \Omega(R,\lambda) J(\lambda) \int_{-F}^{\pi+F} \psi(\lambda,\beta) \Phi(\alpha,\beta,\phi,r,R) \int_{-\infty}^{\infty} h'(\lambda,\alpha) \delta'(\alpha) \Lambda(\alpha,\beta) d\alpha d\beta d\lambda dR$$

where $\rho$ is the radius of the object examined in real space, $\rho^*$ is the equivalent of the radius of the object described in terms of $\lambda$ and $J(\lambda)$ is the Jacobian of the transformation. In this case the Jacobian is the partial derivative of l with respect to $\lambda$.

More precisely:

$$\rho = \lambda \cos(\tan^{-1}\rho^*/D) \quad (8a)$$

$$J(\lambda) \cos^3(\tan^{-1}\lambda/D) \quad (8b)$$

As we indicated above, angle $\beta$ in the data line $h(\lambda,\beta)$ corresponds to the detector position and, because there are a discrete number of detectors, h is not continuous in $\beta$. Because $h(\lambda,\beta)$ will be sampled in $\beta$, a continuum in $\beta$ will be required. Thus, it will be necessary to interpolate h into a continuous function in $\alpha$. This can be done by using an interpolation function $\Lambda$ which can be any one of a number of interpolation functions. One example of an interpolation function which can be used is:

$$\Lambda(\alpha,\beta) = \frac{\sin[\pi(\alpha-\beta)/b]}{\pi(\alpha-\beta)/b} \quad (8c)$$

Thus, $h(\lambda,\beta)$, which is continuous in $\beta$, can be rewritten:

$$h(\lambda,\beta) = \int_{-\infty}^{\infty} h'(\lambda,\beta) \Lambda(\alpha,\beta) \delta'(\alpha) d\alpha \quad (9)$$

where $\alpha$ is the discrete angles corresponding to the detector positions in the physical embodiment and $\beta$ is the continuum of angles corresponding to $\alpha$. Where $$\delta'(\alpha) = \text{Sampler (e.g., } \delta(\sin(\alpha\pi/b))) \quad (9a)$$

$$b = \text{angular displacement between views} \quad (9b)$$

Other interpolators and samplers can, of course, be used provided that compatability between them be maintained.

Introducing a fourier filter function $B(R,\theta)$ which will be equal to 1 inside the Nyquist frequency limit as determined by the spacial sampling rate at the point $(R,\theta)$ and zero outside, substituting the equivalents found in equations (7) and (9) into equation (5), and changing the order of integration, equation (5) can be rewritten as:

$$f(r,\phi) = \int_{-\infty}^{\infty} \int_{-\rho^*}^{\rho^*} \Omega(R,\lambda) J(\lambda) \int_{-F}^{\pi+F} \psi(\lambda,\beta) \Phi(\alpha,\beta,\phi,r,R) \int_{-\infty}^{\infty} h'(\lambda,\alpha) \delta'(\alpha) \Lambda(\alpha,\beta) d\alpha d\beta d\lambda dR \quad (10)$$

where F is one-half the angle of the detector fan beam and:

$$\Omega(R,\lambda) = |R| \exp[-2\pi i R\lambda \cos(\tan^{-1}\lambda/D)] \quad (10a)$$

$$\Phi(\lambda,\beta,\phi,r,R) = B(R, \beta + \tan^{-1}\lambda/D) \exp[2\pi i Rr\cos[\beta + \tan^{-1}(\lambda/D) - \phi]] \quad (10b)$$

and where $\psi(\lambda,\rho)$ is a window function to cut out superfluous angular views defined by:

$$\psi(\lambda,\beta) = 1 \text{ if } -\tan^{-1}\lambda/D \leq \beta \leq \pi - \tan^{-1}\lambda/D \quad (11)$$
$$= 0 \text{ otherwise}$$

As was pointed out earlier, in order to view every point of the scan circle from at least 180°, some points will be viewed from more than 180°. To prevent the superfluous attenuation readings from being used twice, thus giving erroneous sums to be used in computing the final tomographic image values, these extra views are removed. Accordingly, this function sets to zero the attenuation data received along the superfluous beam paths and projected onto the data line. Now, because the redundant angular views have been removed by function $\psi$ and because h was made continuous in $\beta$ in equation (9), it is possible to change the variable of integration from $\theta$ to $\beta$. Changing the variable of integration in equation (10) from $\theta$ to $\beta$ and changing the order to integration, equation (10) can be rewritten:

$$f(r,\Phi) = \int_{-\infty}^{\infty} \int_{-\rho^*}^{\rho^*} \Omega(R,\lambda) J(\lambda) \int_{-\infty}^{\infty} h'(\lambda,\alpha) \delta'(\alpha) \int_{-F}^{\pi+F} \psi(\lambda,\beta) \Lambda(\alpha,\beta) \Phi(\lambda,\beta,\phi,r,R) d\beta d\alpha d\lambda dR \quad (12)$$

or by changing the order of integration once more:

$$f(r,\phi) = \int_{-\infty}^{\infty} \delta'(\alpha) \int_{-\rho^*}^{\rho^*} h'(\lambda,\alpha) J(\lambda) \int_{-F}^{\pi+F} \psi(\lambda,\beta) \Lambda(\alpha,\beta) \int_{-\infty}^{\infty} \Omega(R,\lambda) \Phi(\lambda,\beta,\phi,r,R) dR d\beta d\lambda d\alpha \quad (13)$$

Figure 9:
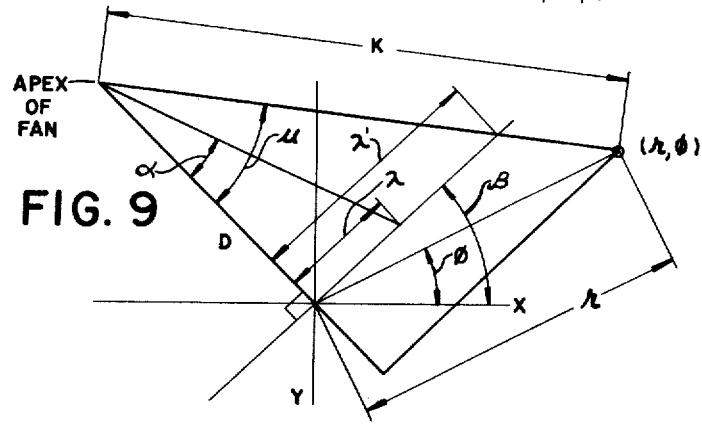
FIG. 9 is a geometric illustration showing another change of coordinates.

In order to get a filter function that looks like a convolution function, the coordinates are changed such that each point within the scan circle is defined by its distance from the apex of the fan and by an angle between center of the fan and a line which connects the apex with the point. This distance will be called $\kappa$ and the angle $\mu$. FIG. 9 illustrates the relationship between $(\kappa,\mu)$ and $(r,\phi)$. Introducing this change of coordinates, the filter function B can be rewritten:

$$B_{\lambda,\beta,r,\phi(R,\theta)} = 1 \text{ for } |R| \leq D/(2ak\cos\mu\cos(\tan^{-1}\lambda/D)) \quad (14)$$
$$= 0 \text{ for } |R| > D/(2ak\cos\mu\cos(\tan^{-1}\lambda/D))$$

If the sampling in $\lambda$ along the data line is done at intervals of a, where a is some positive constant, then it is equivalent to evaluating $h(\lambda,\beta)$ for values of $\lambda$ equal to Na. Defining the last integral of equation 13 as $g(\lambda'-\lambda)$ and substituting for $\Omega$ and $\Phi$ in accord with equations (10a) and (10b) and, further, changing the limits of integration in accord with equation 14, then this last integral can be written as:

$$g(\lambda'-\lambda) = \tag{15}$$
$$\int_{-\infty}^{\infty} \Omega(R,\lambda)\Phi(\lambda,\beta,\phi,r,R)dR =$$
$$\int_{-D/(2a\kappa\cos\mu\cos(\tan^{-1}\lambda/D))}^{D/(2a\kappa\cos\mu\cos(\tan^{-1}\lambda/D))} |R|\exp[2\pi i R\kappa\cos\mu(\lambda'-\lambda)\cos\frac{(\tan^{-1}\lambda/D)}{D}] dR$$

this can be rewritten as:

$$g(\lambda'\lambda) = \tag{16}$$

$$\frac{D^2}{(\kappa\cos\mu)^2\left(\cos\left(\tan^{-1}\frac{\lambda}{D}\right)\right)^2 (\lambda'-\lambda)^2} \int_{-(\lambda'-\lambda)/2a}^{-(\lambda'-\lambda)/2a} |T|\exp(2\pi iT)dT$$

where:

$$T = (\kappa/D)Rt \tag{16a}$$

$$t = (\lambda'\lambda)\cos\mu\cos(\tan^{-1}\lambda/D) \tag{16b}$$

It is apparent that the integral of equation (16) can be evaluated. Thus, performing the integration and choosing $\lambda$ equal to Na, where a is the sampling interval and N is an integer, then:

$$g(M-N) = \frac{D^2 G(M-N)}{4a(\kappa\cos\mu)^2\left(\cos\left(\tan^{-1}\frac{Na}{D}\right)\right)^2} \tag{17}$$

where:

$$G(M-N) = 1 \text{ if } (M-N) \text{ is } 0$$
$$= \frac{4}{\pi^2(M-N)^2} \text{ if } M-N \text{ is odd}$$
$$= 0 \text{ if } M-N \text{ is even}$$

where M is the projection being sampled and N is the total number of projections. Substituting $g(\lambda'-\lambda)$ into equation (13) and replacing the integrals with discrete summations, referring to FIG. (9), it can be seen that:

$$f(r,\phi) = \tag{19}$$
$$\sum_{\alpha=-\infty}^{\infty} \sum_{\lambda=-\rho^*}^{\rho^*} h'(\lambda,\alpha)J(\lambda) \int_{-F}^{\pi+F} \psi(\lambda,\beta)\Lambda(\alpha,\beta)g(\lambda'-\lambda)d\beta$$

$$\kappa(\beta,r,\phi) = [(r\cos(\beta-\phi))^2 + (D+r\sin(\beta-\phi))^2]^{\frac{1}{2}} \tag{20}$$

$$\mu(\beta,r,\phi) = \tan^{-1}(r\cos(\beta-\phi)/(D+r\sin(\beta-\phi))) \tag{21}$$

In order to achieve a spatially invariant and hence computationally feasible convolution function, it is necessary that $g(\lambda'=\lambda)$ be removed from the integral. However, $g(\lambda'-\lambda)$ is a function of $(\beta,r,\phi)$. But note that interpolator $\Lambda(\alpha,\beta)$ is a very narrow function which weights $g(\lambda'-\lambda)$ very strongly for small values of $\alpha-\beta$. For systems with adequate view spacing, errors of less than 0.1% will arise from the following approximation:

$$g(\lambda-\lambda,\beta,r,\phi) \approx g(\lambda'-\lambda,\alpha,r,\phi) = G(\lambda'-\lambda) \tag{22}$$

which is to say that if the detectors are close enough together g can be evaluated as a function of the discrete angle $\alpha$ which marks the position of discrete detectors rather than of the continuous angle $\beta$. Thus, g is always evaluated as of the nearest detector point in this approximation. This, however, allows g to be removed from the integral. With this approximation, equation (19) can be rewritten as follows:

$$f(r,\phi) = \tag{23}$$
$$\frac{D^2}{4a} \sum_{-\infty}^{\infty} \sum_{-\rho^*}^{\rho^*} h'(\lambda,\alpha)\cos(\tan^{-1}\lambda/D) \frac{1}{(\kappa\cos\mu)^2} G(\lambda'-\lambda)\psi^*(\lambda,\alpha)$$

where by previous definition:

$$\psi^*(\lambda,\alpha) = \int_{-F}^{\pi+F} \psi(\lambda,\beta)\Lambda(\alpha,\beta)d\beta$$

$\psi^*$ is simply a convolution of the interpolator $\Lambda$ with the window function $\psi$. It may be applied as a weighting function on the projection data and because the kernal functions can be made stationary $\psi^*$ need only be computed once and simply shifted to the appropriate position on the projection data as determined by $\alpha$. The summation limits on $\alpha$ from minus infinity to infinity are hard to evaluate. However, it is noted that because the interpolator is narrow, $\psi^*$ will remain substantially rectangular similr to $\psi$. If some distance A from the point where $\psi$ goes to zero where chosen and in which $\psi^*$ is sufficiently close to zero, then the limits on equation (23) change from between minus infinity and infinity to between $-F-A$ and $\pi+F+A$. In practice, it has been found that excellent results have been obtained with A equal to zero; thus, equation (23) can be rewritten as follows:

$$f(r,\phi) = \tag{25}$$
$$\frac{D^2}{4a^2} \sum_{\alpha=-F}^{\pi+F} \sum_{\lambda=-\rho^*}^{\rho^*} h'(\lambda,\alpha) \frac{\cos(\tan^{-1}\lambda/D)}{(\kappa\cos\mu)^2} G(\lambda'-\lambda)\psi^*(\lambda,\alpha)$$

where F is one-half the detector fan angle. Thus, the resulting algorithm is simply a convolution and back projection with the addition of a weighting function which is to be applied to the projection data prior to convolution.

Conclusion

It can be seen that with equation 25, the density for each point within the patient circle can be calculated. Thus, a two-dimensional density image $f(r,\phi)$ can be evaluated for all r and $\phi$ within the scan circle and a tomographic image obtained. The above system only needs enough detectors so that each point in the patient circle can be viewed from 180° in order to process the attenuation data into tomographic image. It will be readily apparent that other mathematical approximations can be made and other interpolation functions used to obtain the equation to be evaluated. This invention is not limited to a single interpolation function or approximation; instead, the above interpolation functions and approximations are by way of illustration only. Further, it will be appreciated that the processing and back projection hardware can take many forms in addition to the above-disclosed layout, for example, a digital computer.

The invention claimed is:

1. Apparatus for reconstructing an image of at least a region of an object positioned within a scan circle comprising:
- a source of fan-shaped beam of radiation, said fan-shaped beam rotatable circumferentially about the scan circle by an angle of less than 360°;
- radiation detection means positioned to detect radiation passing from said source through the scan circle and produce sets of electronic data, each set representing the amount of radiation absorbed by a generally fan-shaped region of the object;
- convolver means for performing a convolution operation on at least a part of the sets of electronic data which represent absorption in the fan-shaped regions without binning the electronic data into parallel ray data sets with a convolution function to form convolved data;
- back projecting means for back projecting said convolved data into a memory means; and
- display means operatively connected to said memory means for displaying said image.

2. Apparatus for constructing a representation of the variation of attenuation of penetrating radiation in a planar slice of an object positioned in a scan circle comprising:
- (a) means for generating a plurality of sets of data each set of data representing a characteristic of the attenuation of a fan-shaped swath of radiation passing through the scan circle, each swath having an apex at one of a plurality of angular orientations around said scan circle, said angular orientations of the apices spanning an arc of more than 180° and less than 360°;
- (b) convolver means operatively connected to said means for generating for convolving each set of data with a convolution function to form convolved sets of data; and
- (c) means for transforming the convolved sets of data into said representation.

3. The apparatus as set forth in claim 2 wherein each fan-shaped swath of radiation converges at its apex.

4. The apparatus as set forth in claim 2 wherein said generating means includes a source of a fan-shaped swath of radiation mounted for rotational movement about said scan circle and radiation detection means positioned to receive radiation passing from said source through said scan circle for detecting the radiation and producing elements of electronic data having magnitudes corresponding to the intensity of the radiation detected.

5. The apparatus as set forth in claim 4 wherein said generating means further includes interpolation means for interpolating the elements of electronic data of each set of data into a continuous function whereby each set of data is a continuous function.

6. The apparatus as set forth in claim 4 wherein said convolver means adds to the magnitude of each element of data in each set of data the magnitude of the $N^{th}$ adjacent element of data in the set multiplied by $-4/\pi^2 N^2$ if N is odd and by zero if N is even.

7. The apparatus as set forth in claim 2 wherein said generating means further includes means for removing data from some of said sets of data which removed data corresponds to radiation passing through a point in the scan circle along a path displaced by more than 180° relative to another radiation path through said point.

8. The apparatus as set forth in claim 7 wherein said means for removing includes means for multiplying each set of data by a window function.

9. The apparatus as set forth in claim 8 wherein the window function further adjusts for nonconstant spacing of radiation paths in the fan-shaped swath.

10. The apparatus as set forth in claim 2 wherein the generating means further includes means for multiplying each set of data by a weighting function which weighting function is a function of the angle of the radiation path within the fan-shaped swath corresponding to each data element weighted.

11. The apparatus as set forth in claim 2 wherein said means for transforming the set of data into said representation includes back projection means for back projecting each convolved set of data into a memory means and display means for displaying a visual representation of the data in said memory means.

12. The apparatus as set forth in claim 11 wherein said generating means generates each set of data serially whereby a first set of data is fully generated before generation of a second set is commenced, and wherein said convolver means convolves each set of data serially and wherein said back projection means back projects each convolved set of data serially, whereby as the generating means generates one set of data said convolving means convolves the preceding set of data as said back projection means back projects the penultimate set of data.

13. The apparatus as set forth in claim 11 wherein said memory means has a plurality of memory addresses corresponding to a rectangular matrix of pixel positions.

14. The apparatus as set forth in claim 13 wherein said back projection means further includes means for selecting a data element of a set of data corresponding to each pixel position;
- means for multiplying each selected data element by a weighting function; and
- means for adding the weighted data element to the memory means at the memory address of the corresponding pixel position.

15. The apparatus as set forth in claim 14 wherein said selecting means including means for determining addresses for the set of data by determining differential changes in a subsequent set of data address corresponding to incremental spacing of adjacent pixel positions whereby the selecting means uses an iterative step method to determine the set of data address corresponding to each memory address.

16. Apparatus for constructing a representation of variations in attenuation of penetrating radiation in a planar slice of a body comprising:
- means for generating a plurality of sets of data signals, each set of data signals representing the attenuation of a corresponding array of beams of radiation;
- said means for generating including window means for editing redundant data signals from said sets of data signals;
- back projecting means operatively connected to said means for generating for back projecting edited sets of data signals into a memory; and
- means operatively connected to said memory for constructing said representation.

17. The apparatus as set forth in claim 16 further including convolving means operatively connected between said generating means and said back projecting means for convolving each edited set of data signals with a convolution function whereby the back projection means back projects convolved edited sets of data signals.

18. The apparatus as set forth in claim 17 wherein nonredudant data signals are data signals representing the attenuation of radiation along radiation paths intersecting a point in said planar slice around an arc of less than 180°.

19. Apparatus for back projecting into a memory means a plurality of serially produced sets of data, each set of data having a plurality of data addresses and each set of data having a data value for each data address, said memory means having a plurality of memory addresses, each memory address corresponding to one of a plurality of pixels of a rectangular coordinate pixel matrix, comprising:
 (a) means for iteratively selecting the data address in each set of data corresponding to each pixel position;
 (b) means for determining the data value for each selected data address;
 (c) means for iteratively determining a corresponding weighting function for the data value at each selected data address;
 (d) multiplier means for multiplying each determined data value by the corresponding weighting function;
 (e) adder means for adding the product of said multiplier means to said memory means at the memory addresses which correspond to the same pixel position as the selected data address.

20. The apparatus as set forth in claim 19 further including an interpolator for causing each of said sets of data to have a continuum of data values including a data value for every data address selectable by said selecting means.

21. The apparatus of claim 19 wherein the means for selecting the data address includes means for selecting an initial data address; iterative step means for determining differential changes in the data address for each of the coordinates of the rectangular matrix; and combining means for producing successive data addresses after the initial data position by combining a previous data address with one of said differential changes.

22. The apparatus of claim 19 wherein said sets of data each represent the attenuation of coplanar beams of radiation passing through a substantially planar slice of an object which beams are in fan-shaped arrays of beams, each array having an apex, the apexes arranged at different angular orientations in a circular arc at least partially around the object, each of said plurality of sets of data corresponding to the attenuation of radiation beams in one of the fan-shaped arrays, and wherein each pixel in the rectangular matrix corresponds to a point in said planar slice in the plane of the radiation and wherein the sum in the memory at the memory address represents the attenuation of radiation at the point in the slice corresponding to the same pixel as the memory address.

23. The apparatus of claim 22 wherein said means for selecting the data address includes means for selecting for each one of the sets of data each of the data addresses identified by:

$$(X \cos A - Y \sin A)/(D + X \sin A + Y \cos A)$$

where X and Y are the distance within the object corresponding to the distance between the center of the object and the point corresponding to each of the pixels along each of two perpendicular axes, A is the angular orientation of the apex which the set of data represents and D is the radius of said circular arc.

24. The apparatus of claim 23 wherein the value of said weighting function is $$1/(D + X \sin A + Y \cos A)^2$$

25. The apparatus as set forth in claim 22 wherein said data address selecting means selects as the $n^{th}$ data address $$S_n/E_n$$

where n is an integer and $$S_n = S_{n-1} - \cos A$$

$$E_n = E_{n-1} + \sin A$$

where A is related to the angular orientation represented by the set of data and $$E_o = D + X_o \sin A + Y_o \sin A$$

$$S_o = (X_o \cos A - Y_o \sin A)/E_o$$

where D is a system constant and $X_o$ and $Y_o$ are related to the coordinates of the initial pixel position.

26. The apparatus of claim 19 further including a display means for producing a visual display made up of a rectangular array of display pixel points, the display means being operatively connected to said memory means, each display pixel point corresponding to one of said matrix pixels and wherein each display pixel points displays a degree of shading which is related to the sum in said memories at the corresponding memory address.

27. The apparatus as set forth in claim 19 further including means for generating data values representing a characteristic of the attenuation of a fan-shaped swath of radiation passing through a scan circle, each swath having an apex at one of a plurality of angular orientations around said scan circle; said generating means including sorting means for sorting said data values into sets; and convolver means for convolving each set with a convolution function for producing said serially produced sets of data.

28. The method of reconstructing an image of radiation attenuation in a planar region of an object comprising the steps of:
 irradiating said planar region with a planar fan-shaped swath of radiation;
 rotating said swath circumferentially about said planar region through an angle of less than 360°;
 detecting the radiation passing through the planar region and producing sets of electronic data, each set representing the intensity of detected radiation absorbed by a generally truncated fan-shaped region of the object;
 performing a convolution operation on at least part of said sets of electronic data without binning the electronic data into parallel ray data sets with a convolution function to form convolved data;
 back projecting said convolved data to form a plurality of sums, each sum representing the attenuation of radiation at a point in said planar region; and
 displaying said sums to form said image.

29. The method as set forth in claim 28 further comprising the steps of sorting the electronic data by angular position of the apex of said swath to form the set of data; sorting the data within each set of data by the angular position with said swath; and interpolating each set of data to form a continuous data function for convolving.

30. The method as set forth in claim 29 further comprising the step of multiplying each continuous data function by a window function to remove redundant data before convolving the continuous data function to form a convoluted data function.

31. The method as set forth in claim 30 wherein said back projecting step further includes selecting an initial address in a convolved data function; weighting the data value at said initial address; adding said data value to a sum corresponding to one of plurality of points in a rectangular matrix array in said planar region; selecting a subsequent address as a function of the initial address and the incremental spacing between adjacent points in the rectangular matrix; and repeating the selecting a subsequent address, weighting and summing for each point in the rectangular matrix.

32. The method of back projecting sets of data, each set of data having a plurality of data addresses and each set of data having a data value at each data address into a memory, said memory having a plurality of addresses corresponding to a rectangular coordinate matrix, comprising the steps of:
  (a) providing a set of data;
  (b) selecting a data address corresponding to a coordinate of the rectangular coordinate matrix;
  (c) determining a data value from said data address;
  (d) determining a weighting function corresponding to said data address;
  (e) multiplying said data value by said weighting function to produce a weighted data value;
  (f) adding said weighted data value to the memory at the memory address corresponding to said coordinate of the rectangular coordinate matrix;
  (g) iteratively determining another data address by adding to the previous data address a function the spacing corresponding to the coordinates of the rectangular matrix;
  (h) determining another data value from the another data address;
  (i) iteratively determining another weighting function corresponding to another data address;
  (j) multiplying said another data value by said another weighting function to produce another weighted data value;
  (k) adding the another weighted data value to the memory at the corresponding memory address;
  (l) repeating steps (g) through (k) for a plurality of data addresses; and
  (m) repeating steps (a) through (l) for at least a plurality of serially produced sets of data.

33. Apparatus for back projecting into a memory means a plurality of serially produced sets of data, each set of data having a plurality of data addresses and each set of data having a data value for each data address, said memory means having a plurality of memory addresses each memory address corresponding to one of a plurality of pixels of a rectangular coordinate pixel matrix, comprising:
  (a) geometric value determining means for iteratively determining a geometric value;
  (b) data address selecting means for iteratively selecting the data address in each set of data corresponding to each pixel position, the data address selecting means being operatively connected to said geometric value determining means;
  (c) data value determining means for determining the data value for each selected data address, the data value determining means being operatively connected to said data address selecting means;
  (d) weighting function determining means for determining a corresponding weighting function for each data address, the weighting function determining means being operatively connected to said geometric value determining means;
  (e) multiplier means for multiplying each determined data value by the corresponding weighting function, the multiplier means being operatively connected to said data value determining means and said multiplier means; and
  (f) adder means for adding the product of said multiplier means to said memory means at the memory addresses which correspond to the same pixel position as the selected data address, the adder means being operatively connected to said multiplier means and said memory means.

* * * * *